(12) United States Patent
Bareket et al.

(10) Patent No.: US 6,614,520 B1
(45) Date of Patent: Sep. 2, 2003

(54) METHOD FOR INSPECTING A RETICLE (75) Inventors: Noah Bareket, Saratoga, CA (US);
Christian G. Desplat, London (GB);
Lance A. Glasser, Saratoga, CA (US)

(73) Assignee: Kla-Tencor Corporation, San Jose, CA (US)

( * ) Notice: Subject to any disclaimer, the term of this patent is extended or adjusted under 35 U.S.C. 154(b) by 591 days.

(21) Appl. No.: 08/993,107

(22) Filed: Dec. 18, 1997

(51) Int. Cl.7 ................................................ G01N 21/88
(52) U.S. Cl. ..................... 356/237.3; 350/394
(58) Field of Search ................... 356/394, 398, 356/237.3, 237.4, 239.8

(56) References Cited

U.S. PATENT DOCUMENTS

| | | | |
|---|---|---|---|
| 3,909,602 A | * 9/1975 | Micka | ........................ 356/394 |
| 4,772,127 A | 9/1988 | Chase et al. | |
| 4,794,264 A | 12/1988 | Quackenbos et al. | |
| 4,898,471 A | 2/1990 | Stonestrom et al. | ........ 356/394 |
| 4,943,734 A | 7/1990 | Johnson et al. | |
| 5,058,982 A | 10/1991 | Katzir | |
| 5,076,692 A | 12/1991 | Neukermans et al. | |
| 5,098,191 A | * 3/1992 | Noguchi et al. | ............. 356/394 |
| 5,153,668 A | 10/1992 | Katzir et al. | |
| 5,355,212 A | 10/1994 | Wells et al. | |
| 5,389,794 A | 2/1995 | Allen et al. | |
| 5,563,702 A | 10/1996 | Emery et al. | |
| 5,572,598 A | 11/1996 | Wihl et al. | |

OTHER PUBLICATIONS

Handbook of Microlithography, Micromachining, and Microfabrication, vol. 1: Microlithography; Chapter 5, "Photomask Fabrication Procedures and Limitations", pp. 377–385, and pp. 469–474, by Skinner et al., 1997.

* cited by examiner

Primary Examiner—Richard A. Rosenberger
(74) Attorney, Agent, or Firm—Beyer, Weaver & Thomas, LLP.; Mary R. Olynick, Esq.

(57) ABSTRACT

Disclosed is a method of inspecting a reticle for defects that occur over time. The invention accomplishes this by generating and storing a "baseline" image of the reticle and then periodically generating a "current" image of the reticle and comparing the current and baseline images. The baseline image is taken at a time when the reticle is known to be acceptable. This may be when the reticle has been "qualified" by an optical test or when a die fabricated by reticle has passed an electrical test. Also disclosed in a method for compacting the baseline image before storage.

26 Claims, 6 Drawing Sheets

METHOD FOR INSPECTING A RETICLE

BACKGROUND OF THE INVENTION

The present invention relates to systems for determining whether a reticle is defective. More particularly, the present invention relates to systems and methods which identify reticle defects that arise at some time after a reticle is "qualified" as being suitable for use.

A normal reticle or photomask is an optical element containing transparent and opaque regions which together define the pattern of coplanar features in an electronic device such as an integrated circuit. A phase shift reticle, which is also well known in the art, may further include graded regions (with varying thickness) that cause a phase shift of the transmitted light. In order to learn more about phase shift reticles, reference may be made to book authored by Van Zant, Peter, entitled "Microchip Fabrication" McGraw-Hill, 1997, which is incorporated herein by reference for all purposes. Reticles are used during photolithography to define masks which protect specified regions of a semiconductor wafer from etching, ion implantation, or other fabrication process. For many modern integrated circuit designs, a reticle's features are between about 4 and about 20 times larger than the corresponding feature size of the mask on the wafer.

Reticles are typically made from a transparent medium such as a borosilicate glass or quartz plate on which is deposited an opaque pattern of chromium or other suitable material. The reticle pattern may be created by a laser or an e-beam direct write technique, for example, both of which are widely used in the art. The reticle is framed and covered by a pellicle which is a thin layer of an optically neutral material such as a polymer attached to the frame. Typically, an adhesive is used to affix the pellicle to the frame. Once in place, the pellicle (positioned about 6 mm from the reticle) protects the reticle from dirt or dust particles in the environment. Such particles may deposit on the pellicle but do not affect the reticle's image because the pellicle is located beyond the focal plane of the reticle.

During the normal course of the reticle's life, however, defects can be introduced into the reticle. For example, particles may be present but hidden (on the chromium region for example) when the reticle is initially formed. Over the course of time, some of these particles may migrate onto the transparent regions where they degrade the image quality. In another example, defects may be introduced into the reticle by "flaking" of the frame or the adhesive material that affixes the pellicle to the frame.

In yet another example, an electrostatic discharge (ESD) generated by a stepper apparatus employed during conventional photolithography may damage the opaque regions of the reticle.

If a reticle becomes defective due to one of the above mechanisms, for example, it may have a very negative impact on the yield of an IC fabrication facility. For example, a particle spanning two opaque lines on a reticle may result in shorting between adjacent metal or polysilicon lines. Other reticle defects may cause more subtle defects that can not easily be detected and may not be manifested until the ICs are in the customers' hands. Undetected, such defects can cost a facility many millions of dollars and potential embarrassment. Thus, many IC manufactures periodically image or otherwise test their reticles to ensure that they are not defective.

Figure 1A:
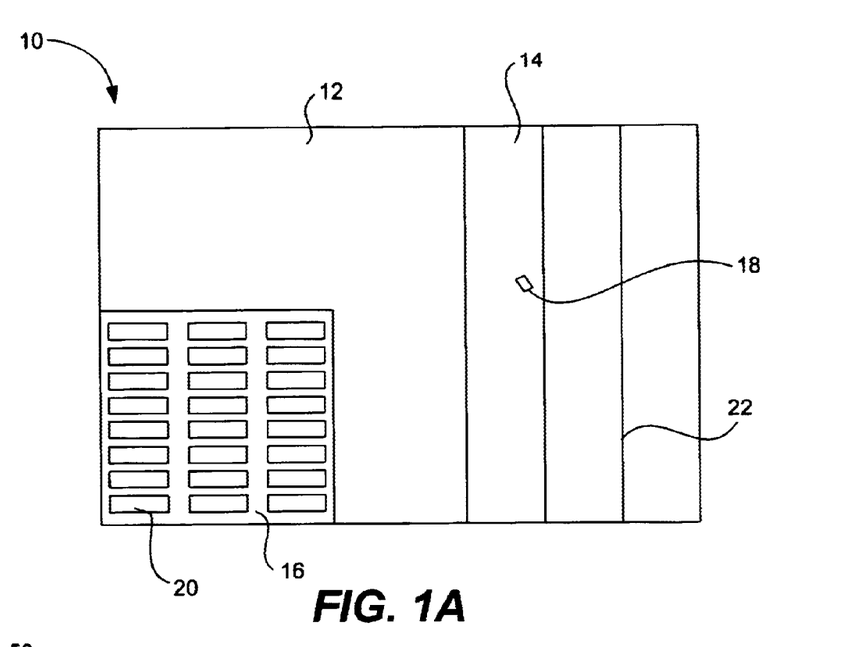
FIG. 1A shows an idealized representation of an image of a reticle that may be used to identify defects according to the present invention.

FIG. 1A is an idealized representation of an actual "darkfield" image 10 of a reticle obtained by scanning a light beam onto the reticle and monitoring light scattered therefrom. In the actual image, various regions of the image have varying shades of gray. In FIG. 1A, the various shades of gray could not be accurately depicted, so the contrast between features is exaggerated in some cases and reduced in other cases.

Image 10 of the reticle has a dark area 14, a bright area 16, and a very dark area 12. Areas 14 and 16 have certain relatively bright repetitive features created by light scattering off of valid repetitive features on the reticle surface. For example, dark area 14 includes vertical lines 22 created by some repetitive feature on the reticle. Such image patterns created by valid structures may fool a detector into believing that they constitute defects. Therefore these features are sometimes referred to herein as "false defects." In addition to vertical lines 22, dark area 14 also has a random bright spot 18 indicative of a reticle defect (hereinafter referred to as a "real defect"), which may be caused by an electrostatic discharge (ESD) for example.

Bright area 16 receives its brightness from bright bands 20 which are light scattered off of valid die features (more examples "false defects"). Very dark area 12 contains very little scattered light and no bright spots that would represent real or false defects on the reticle.

As should be apparent from a study of FIG. 1A, various real and false defects may appear in an image. Obviously, a test system must be able to separate the real from the false. Traditionally, this has been accomplished by employing a "die-to-die" comparison which may be carried out in KLA 301 or 351 Reticle Inspection Tool, commercially available from KLA-Tencor of San Jose, Calif.

In systems employing the die-to-die approach, the images of two supposedly identical patterns on a reticle are compared. Note that many reticles contain the patterns of multiple identical die, collectively referred to as a field. Images of two or more of these individual die patterns in a field are compared by optically overlaying the patterns. Such comparisons will screen the false defects because they will be found on the images of both die. Real defects presumably occur randomly and therefore appear only on a single die. Thus, a comparison of two die pattern images will normally find a real defect on only a single die pattern. Thus, the imaging system will flag bright spots appearing on only a single image as real defects.

Figure 1B:
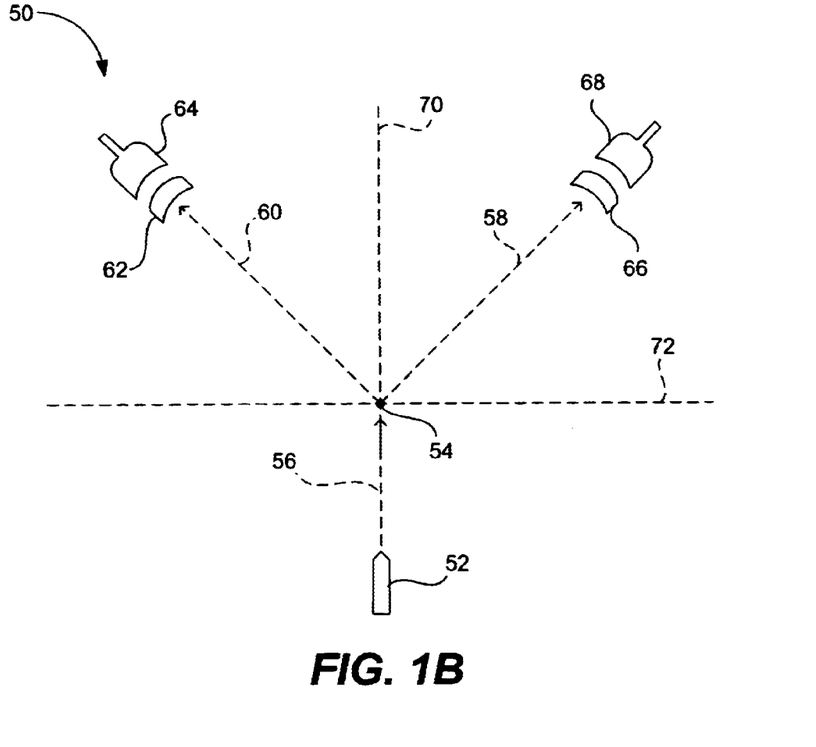
FIG. 1B shows a top view of some significant components of a darkfield detector that may be employed to scan and generate an image of a portion of a reticle.

FIG. 1B shows some significant components of a scattering or "darkfield" detecting assembly 50 that may be employed to scan a reticle surface and generate an image of the reticle or die pattern. An incident beam 56 generated by an illuminating source 52, e.g., a laser, is directed at a portion of a reticle surface 54. Incident beam 56 travels along an incident axis 70 and perpendicular to an axis 72. First and second detectors 64 and 68, positioned at an oblique angle, e.g., 45°, with respect to the incident axis 70, detect a first and second scattered energy signals 58 and 60, respectively, from reticle portion 54 after the scattered energy signals pass through filters 62 and 66.

During a typical inspection process of reticle portion 54, illuminating source 52 directs incident beam 56 to strike reticle portion 54 and a resulting scattered light signal is detected by first and second detectors 64 and 68. A defect residing at reticle portion 54 may, therefore, be flagged, if the intensity of the detected light signal is equal to or exceeds a predetermined threshold signal intensity. If, however, the intensity of the scattered energy signal detected is less than a predetermined threshold signal intensity, then reticle portion 54 is considered to be free of defects.

Typically, the source and detectors are moved in a rasterized fashion to generate an image of the entire reticle.

During a die-to-die comparison in the same reticle, it may be difficult to discriminate between false defects and true defects. This is because there may be subtle differences between the dies that are not necessarily true printable defects. For example, small differences in feature width may fall within acceptable tolerances but still show up as defects on die-to-die comparisons. Further, some reticles contain a pattern for a single die only. Obviously, in such cases die-to-die reticle inspection can not be implemented.

What is needed is an improved inspection system that rapidly and inexpensively determines whether a defect has appeared in a reticle.

SUMMARY OF THE INVENTION

The present invention provides a method of inspecting a reticle for defects that occur over time. The invention accomplishes this by generating and storing a "baseline" image of the reticle and then periodically generating a "current" image of the reticle and comparing the current and baseline images. The baseline image is taken at a time when the reticle is known to be acceptable. Often this is when the reticle has been "qualified" by an optical test or a die fabricated by reticle has been electrically tested. Because the comparison relies upon images of the exact same portions of the reticle, the problems inherent in die-to-die techniques are avoided.

In some cases, the methods of this invention may be characterized by the following sequence: (a) providing a baseline image of the reticle which was created while the reticle was qualified as being of acceptable quality; (b) generating a current image of the reticle (preferably in the same manner as the baseline image); and (c) comparing the baseline and current images to identify any new defects that may have arisen in the time between when the baseline image was created and when the current image is generated.

The baseline and current images may be obtained by scanning the surface of the reticle with light from an illumination source. For each region considered in the scan, the method may involve (i) illuminating a region of the reticle by an incident beam generated by an illuminating source; (ii) detecting a scattered energy distribution from the region of the reticle by a detector; and (iii) recording the scattered energy distribution from the region of the reticle.

The baseline and current images may be compared by a process involving first determining whether intensity of scattered radiation at a first location of the current image is greater than a defined threshold; and if so, then determining whether a corresponding region of the baseline image also contains scattered radiation of substantially the same intensity. The initial comparison of the current image with a threshold speeds the overall comparison. If a particular portion of the current image does not exceed the threshold, then no significant scattering occurred there which means that the no defect resides there—regardless of any comparison to the baseline image. If a direct comparison of the baseline and current images is necessary, then those regions where the intensity value of the current image significantly exceeds the corresponding intensity value of the baseline image are deemed to contain a defect.

Various techniques may be employed to facilitate the general methods of this invention. For example, the baseline image may be compacted to reduce the quantity of stored data for portions of the image where the intensity of the scattered radiation does not exceed a defined threshold. In a preferred embodiment, compacting includes the following: (i) segmenting the baseline image into regions of the reticle; and (ii) removing data from the baseline image for those regions of the reticle where the intensity of the scattered radiation does not exceed the defined threshold.

In addition, multiple imaging algorithms may be employed to image various regions of the reticle under evaluation. For each region, a best algorithm is selected. This best algorithm is better able to discriminate between real and false defects than any other algorithms. In one embodiment, a suitable method includes the following sequence: (a) providing the reticle to be inspected; (b) generating data specifying intensity of radiation scattered from the reticle as a function of location on the reticle; (c) defining a first portion of the data which was derived from a first region on the reticle; (d) applying a plurality of imaging algorithms to the first portion of the data; (e) selecting a first imaging algorithm from among the plurality of imaging algorithms based upon ability to suppress scattered radiation from valid features on first region of the reticle; and (f) associating the first imaging algorithm with the first portion of data in the baseline image, such that during the subsequent inspections of the reticle the first imaging algorithm is applied to the first portion of the data to provide an image of the first region of the reticle. Generally, the method will also involve storing in memory an association of the first imaging algorithm with the first region of the reticle. In addition, the various imaging algorithms may be ranked according to ability to suppress scattered radiation from valid features on the reticle.

In some embodiments, the image data is generated in multiple passes. In such embodiments, the process may involve the following: (I) carrying out a first scan of the reticle under a first apparatus setting for determining intensity of radiation scattered from the reticle as a function of location on the reticle; (ii) carrying out a second scan of the reticle under a second apparatus setting which are different from the first apparatus setting; and (iii) selecting an apparatus setting based upon ability to suppress scattered radiation from valid features on the reticle. Preferably, (iii) is performed for each of a plurality of regions of the reticle. Thus, the system will associate a selected apparatus setting with one or more regions of the reticle, such that during the subsequent inspections of the reticle data from the selected apparatus setting may be used to image the one or more regions.

These and other advantages of the present invention will be described in more detail below in the detailed description of the invention and in conjunction with the following figures.

DETAILED DESCRIPTION OF THE PREFERRED EMBODIMENTS

The present invention provides a process of identifying defects in a reticle that arise over time—typically while the reticle is in operation—by comparing an image of the reticle with a baseline image of the reticle when it was qualified. In the following description, numerous specific details are set forth in order to fully illustrate a preferred embodiment of the present invention. It will be apparent, however, that the present invention may be practiced without limitation to some specific details presented herein.

Figure 2A:
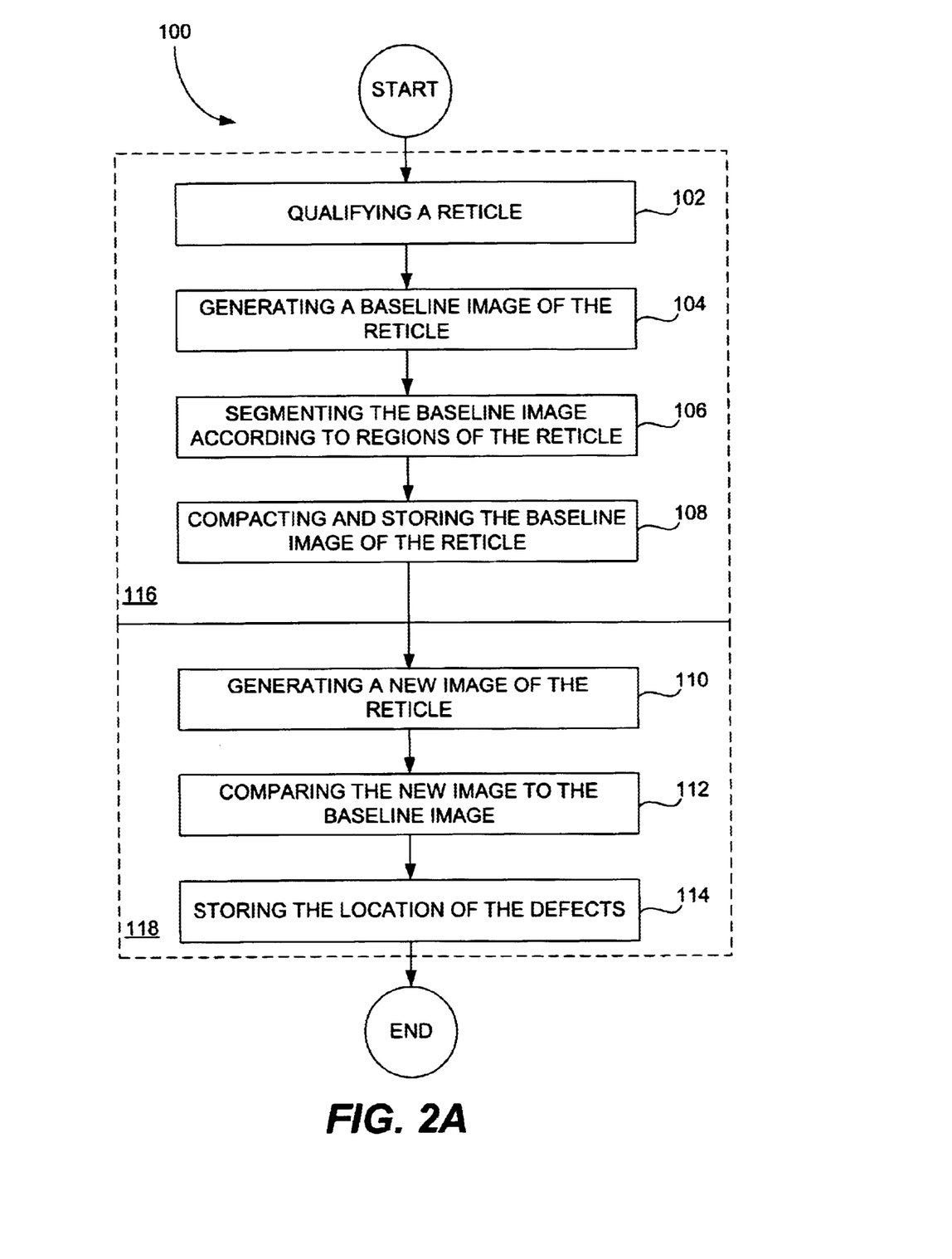
FIG. 2A shows a flowchart, according to one embodiment of the present invention, ,of a process of determining whether a defect has appeared in the reticle.

FIG. 2 shows a flowchart of a process 100 for identifying reticle defects that arise during the life of a reticle. The process is divided into two phases: a baseline image generating phase 116 and a comparison phase 118. Baseline image generation phase 116 may begin at a step 102 that includes qualifying a reticle, a baseline image of which will subsequently be generated. A reticle is "qualified" when it is known to be of acceptable quality. This means that the reticle is deemed sufficiently free of problematic defects that it can be used with confidence during photolithography. As a result, a qualified reticle should not be responsible for a relatively low yield or other problem with the electronic devices fabricated by using of the reticle.

After the reticle is qualified, a baseline image of the qualified reticle is generated at a step 104. Step 104 may be carried out using an inspection apparatus such as the scattered light detecting assembly shown in FIG. 1B. In this step, the intensity of the energy scattered from an illuminated reticle surface is measured and recorded, pixel-by-pixel, as described above in the discussion pertaining to FIG. 1B. In one embodiment, this may be carried out by scanning the reticle surface in a single pass, during which the settings of the illuminating source and detectors are fixed. In another embodiment, this may be carried out by scanning the reticle in multiple passes, with the machine settings varying from one scan to another. By way of example, one scan may have different oblique angles of first detector 64 and second detector 68 with respect to the incident axis 70 than in another scan. As will be explained later, different settings of the illumination source and detectors may facilitate distinguishing between a real defect and false defect in different regions of a reticle.

Generally, step 104 is carried out contemporaneously with the step of qualifying the reticle. The term "contemporaneously," as used in connection with the description of this invention means that the baseline image of the reticle is generated relatively soon after the reticle is qualified or after any period of time, e.g., a few minutes to a few days or more, when it is reasonable to believe that no new defects have been introduced into the qualified reticle.

Next, in a step 106, the baseline image of the reticle is divided into various segments, each of which corresponds to a separate region on the reticle. The term "region," as used herein, refers to a relatively small section of the reticle. By way of example, very dark area 12, dark patterned area 14 and bright patterned area 16 of FIG. 1A each may be divided into several regions. At the extreme, each region or segment corresponds to a separate pixel. Typically, the regions will comprise at least a few pixels. To facilitate processing of image data, each region within an area of a reticle is assigned an address and an intensity value (for the scattered radiation).

Next, in a step 108, the baseline image of the reticle generated in step 104 is optionally compacted by reducing the quantity of image data for those regions of the reticle that do not include a real defect or a false defect (i.e., those regions without any features or defects that scatter radiation to a level exceeding a threshold as measured by the detector (s)). By way of example, much of the scattering data for the very dark area 12 (which falls below the threshold for indicating a defect) may be deleted in this step. All that would remain are data defining the coordinates of the boundaries of area 12.

Baseline generation phase 116 concludes with the system storing the baseline image in either a compacted or uncompacted form. In the above example, the stored baseline image includes detailed intensity data for dark pattern area 14 and bright pattern area 16 but very little, if any, intensity data for area 12.

By using compaction to reduce the data quantity in the baseline image, the memory storage space required to store the baseline image is significantly reduced. Depending upon the image, compaction may reduce the stored data from on the order of gigabytes to on the order of megabytes, for example. Further, a compacted baseline image speeds up the comparison step, which is described hereinafter.

The next phase of the process, comparison phase 118, takes place some time after baseline generation phase 116. Generally, it will take place after there is reason to believe that the reticle could have become defective. For example, a comparison may be appropriate after the reticle has been used for a certain number of photolithography operations or has been in existence a certain length of time. Alternatively, a comparison may take place when the reticle has been subjected to a potentially damaging event (e.g., mishandling). In any event, its purpose is to determine whether any new defects have arisen in the time since the reticle was qualified (deemed acceptable).

Comparison phase 118 begins with the system generating a new image of the reticle at a step 110. This new image may be generated by scanning the reticle surface with a light beam and measuring the intensity of the scattered light as a function of position. This step may be performed in the manner described with reference to step 104. While not critical to the practice of this invention, it will generally be desirable to employ the same scattered light detecting assembly and apparatus settings as employed to generate the baseline image. This will facilitate comparison of the two images. In this step, the new image of the reticle may be stored in memory for subsequent comparison.

In a step 112, the baseline image generated in step 104 is compared with the new image of the same reticle in step 110. The purpose of this step is to identify any new defects indicating that the reticle should be retired. Next, in a step 114, the location of any real defect(s) found during comparison step 112 is stored in memory. This may simply involve marking the address of the defect location as containing a real defect. The stored information may be evaluated by other software to determine whether the new defect's type or location is sufficiently problematic that the reticle should be retired or repaired. If the software concludes that the reticle need not be replaced, then the new image may be preserved for comparison with subsequently taken images. In such comparison, the new defect will not cause alarm. After step 114 is completed the comparison process ends.

QUALIFICATION

As mentioned above, the baseline image is taken while the reticle is believed to be acceptable. Typically the reticle will be known to be acceptable because it has been qualified. Thus, in process 100, the reticle is qualified at step 102. Qualification may be accomplished in a number of different ways known to those of skill in the art. In one case, the reticle undergoes a rigorous optical examination to identify any defects, a priori. If the number and/or type of defects indicates a problem, the reticle is rejected. By way of example, if more than about 10 potential defects are identified, the reticle is rejected.

In one specific embodiment, the reticle is qualified with the KLA STARlight inspection system available from KLA-Tencor Corporation of San Jose, Calif. This and similar inspection systems analyze a reticle pixel-by-pixel by scanning the reticle with an illumination source and monitoring the transmitted and reflected light. By accounting for the reflectivity and transmittance of glass and chrome or other material employed in the reticle, the system constructs a very accurate and detailed image of the reticle from scan data. While such optical techniques unambiguously qualify a reticle, they are slow and expensive. Therefore, it is impractical to use them to periodically evaluate a working reticle.

A reticle may also be qualified by an electronic test. In such cases, a die fabricated with the reticle under consideration is subjected to a rigorous electrical test or battery of tests to confirm that it is operating according to specification. If the die passes the test(s), it can be assumed that the reticle (as well as every other piece of apparatus in the fabrication process) is acceptable.

BASELINE IMAGE GENERATION

As mentioned in the discussion of step 104, a baseline image is generated for the purpose of providing an image of the reticle while in a qualified state. Later, the system compares this baseline image to a new image of the reticle in order to identify any new defects. The baseline image is necessary because many valid features on the reticle scatter light nearly as strongly as—if not as strongly as—real defects. In order to clearly distinguish between scattering from valid structures (false defects) and scattering from real defects, the system needs to compare the two images.

Briefly, the intensity of a scattered energy signal of a reticle feature (or defect) is highly dependent on the geometry and environment of that feature, e.g., the density of the lines at the reticle feature and the angle of these lines with respect to the incident axis and the oblique angle of the scattered light detectors, etc. If the density of lines of the die feature is relatively high, i.e. the distance separating the lines is small, the intensity of scattered light signal can be significant.

COMPACTION

Figure 2B:
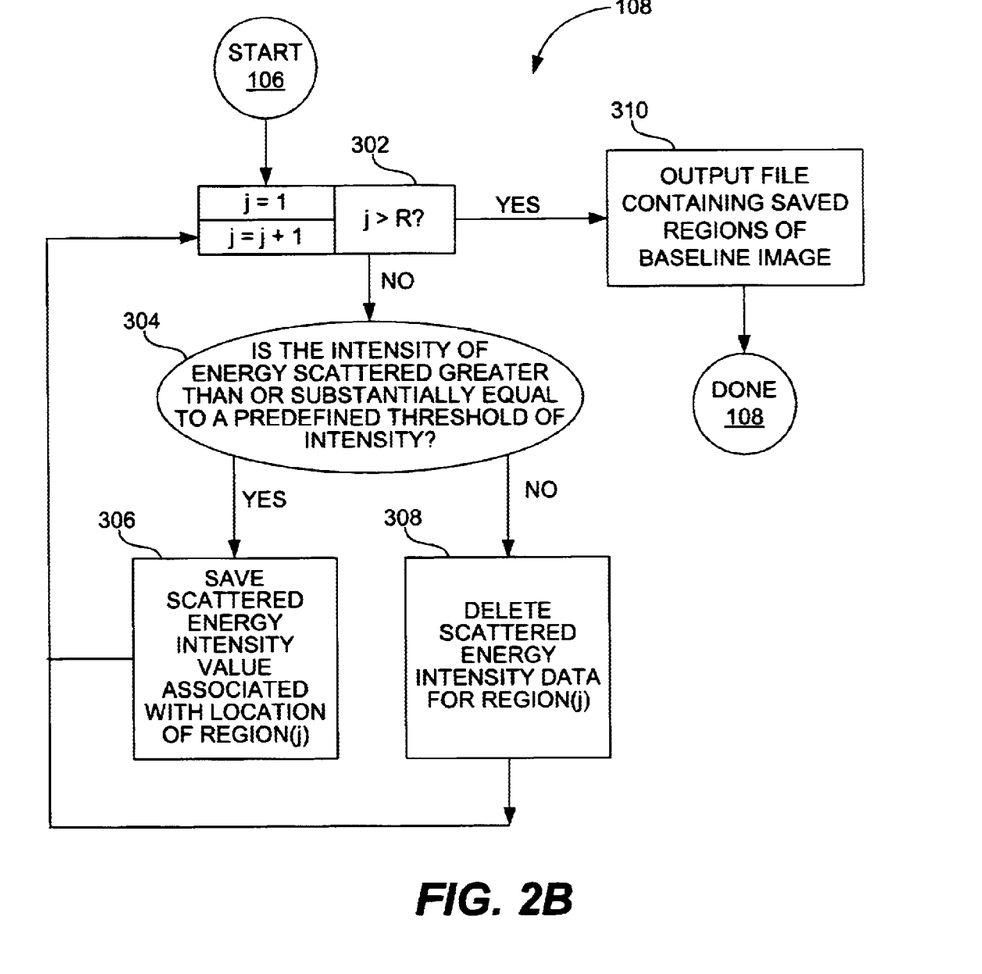
FIG. 2B shows a flowchart, according to one embodiment of the present invention, of a process for compacting a baseline image of a reticle.

FIG. 2B illustrates one approach to implementing step 108 of process 100 (i.e., compacting a baseline image). Process 108 begins with an iterative loop step 302, in which "j" is an index denoting a particular domain or region of the reticle (obtained during segmenting step 106) and "R" denotes the total number of regions present in the reticle. Iterative loop step 302 initially sets the value of j to 1. This specifies the first region of the baseline image to be considered. Subsequently, step 302 increments the value of j successively until it exceeds the value of R.

After selecting the region having the current index, j, the system determines whether the intensity of scattered radiation recorded for that region is greater than a predefined threshold of intensity. See step 304. If so, the system stores in memory the intensity value of the scattered light and its location. See step 306. If, however, the intensity of scattered light recorded for the region under consideration is not greater than the predefined threshold, then the intensity data for that region is not saved or is deleted. See step 308. However, the coordinates of the region are noted so that the bounds of the "dark" region can ultimately be delineated.

After either step 306 or 308 is completed, process control returns to iterative loop step 302, where the value of index j is incremented by 1. Assuming that the value of j is still less than R, decision step 304 is reexecuted for the new region under consideration. After the intensity data of all regions has been processed as described in steps 304, 306 and 308 (i.e., j is greater than R), an output file containing saved regions of the baseline image is generated in a step 310. Process 100 then proceeds to step. 108 as described above. Note that the output file also delineates the boundaries of any dark regions for which reduced or no intensity data is maintained.

COMPARISON

The process of comparing the new and baseline images (step 112 of process 100) may begin with a sequential examination of pixels or other small domains of the new image. For each pixel or domain, the system determines whether the intensity of scattered radiation is greater than a predefined threshold of intensity (preferably the threshold set for step 108). If the intensity does not exceed the threshold, then the system moves to the next pixel where the intensity of scattered light is considered. If, on the other hand, the intensity does exceed the threshold, then the system determines whether a false defect (bright spot) is present in the corresponding pixel of the baseline image. Should a similarly bright spot be present in the baseline image, it is assumed that the radiation was scattered by a valid feature (false defect). Should no corresponding bright spot reside in the baseline image, the system concludes that a real defect may be present and saves the intensity and location information.

Figure 2C:
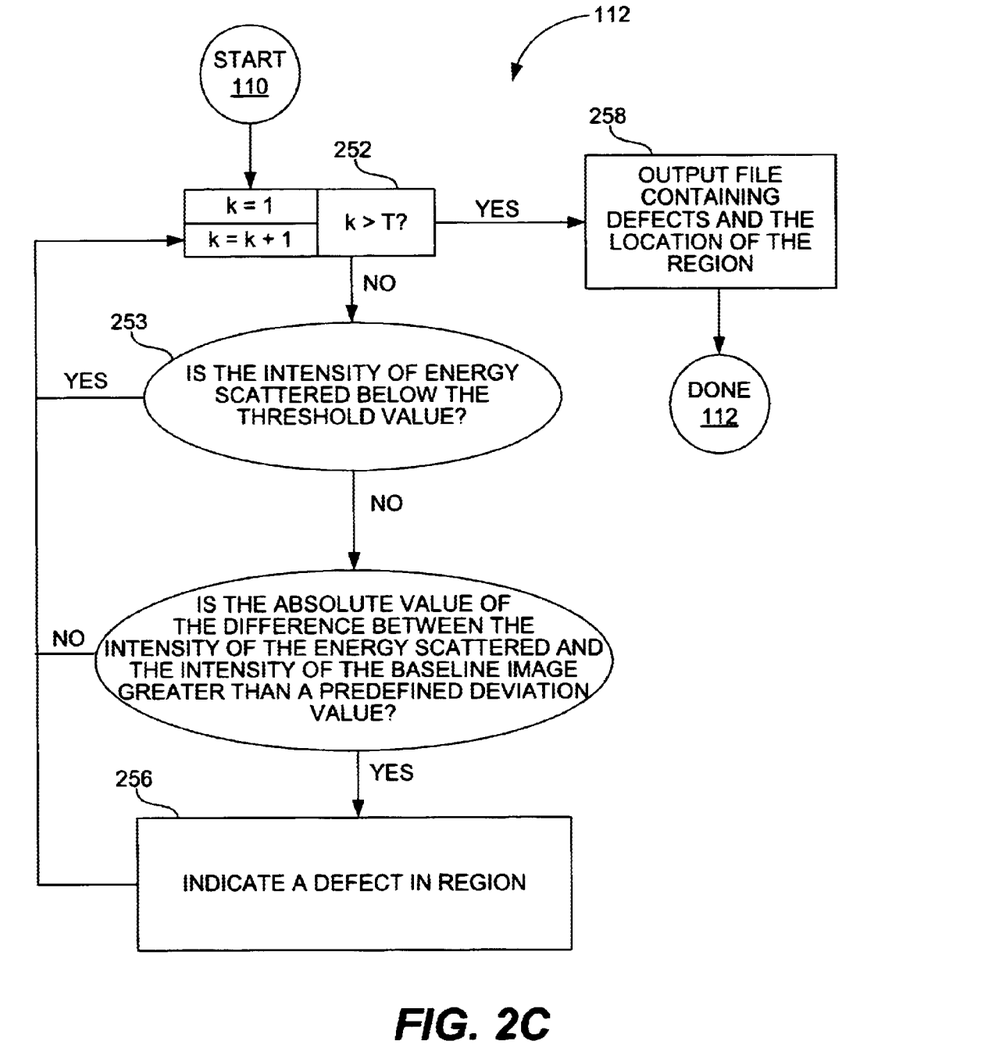
FIG. 2C shows a flowchart, according to one embodiment of the present invention, detailing a process of comparing a current image to a baseline image of a reticle.

FIG. 2C shows one process flow for implementing step 112 of process 100. The step of comparing the baseline image to the new image of the reticle begins at an iterative loop step 252, in which "k" is an index denoting the particular region of the reticle under consideration and "T" denotes the total number of regions present in the reticle. Often the value of T will equal the value of R (FIG. 2B). Iterative loop step 252 initializes the value of k to 1, compares the current value of k to T, and directs process control to a decision step 253 when k is less than or equal to T.

In decision step 253, the system determines whether the intensity reading of the region under consideration exceeds the threshold value. If not, no defect resides in the region, and process control returns to step 252, where the value of k is incremented by 1. However, if the intensity reading of the region under consideration exceeds the threshold, then process control is directed to a comparison step 254. In step 254, the system determines whether the absolute value of the difference in intensity of scattered light in the new image of a region and the intensity of scattered light in the baseline image of the region exceeds a predefined deviation value. If so, a real defect is indicated and the system marks the region as containing a defect at a step 256. Thereafter process control returns to step 252 where the value of k is incremented by 1. If the system determines that the absolute value of the difference in intensity of scattered light in the new image of a region and the intensity of scattered light in the baseline image of the region does not exceed a predefined deviation value (i.e., step 254 is answered in the negative), then it is established that there are no new real defects present in the reticle.

After R number of regions of the reticle are examined as described above, an output file containing real defects and their location or the address of their region is generated in step 258. Process 100 then proceeds to step 114 as described with reference to FIG. 2A.

It may be noted that in the event the region under consideration was compacted in step 108, then the comparison performed in step 254 employs a null value of scattered light intensity. This means that any detector reading above the threshold in such regions will be considered to represent a real defect.

TRAINING ALGORITHMS

An image (baseline or new) may be generated from detector data by any of a number of algorithms. The simplest algorithm presents each pixel of an image exactly as the intensity read by a detector for the corresponding point on the reticle. If there are two or more detectors, then the average of their readings may be employed. In more complex algorithms, the image value of any given pixel may be influenced by the detector readings a group of neighboring locations on the reticle. For example, some form of interpolation may be employed. Other algorithms may employ functions to weight the contributions to the image that the various detectors make for any given pixel.

The goal of any of these algorithms is to discriminate between real and false defects. For a given detector setting and reticle pattern, some algorithms will do a better job than others. Because reticle patterns vary in density, shape, and angle over the surface of the reticle, it is not surprising that an algorithm that works best at one region of the reticle will not work best at some other region of the reticle. Thus, a preferred embodiment of the invention employs determines which of a plurality of imaging algorithms works best for any given region of the reticle image. The end result, is a mapping of imaging algorithms to regions of the reticle image. Then during reconstruction of the image, the imaging algorithm mapped to a given region is used to generate the image of that region.

Figure 3:
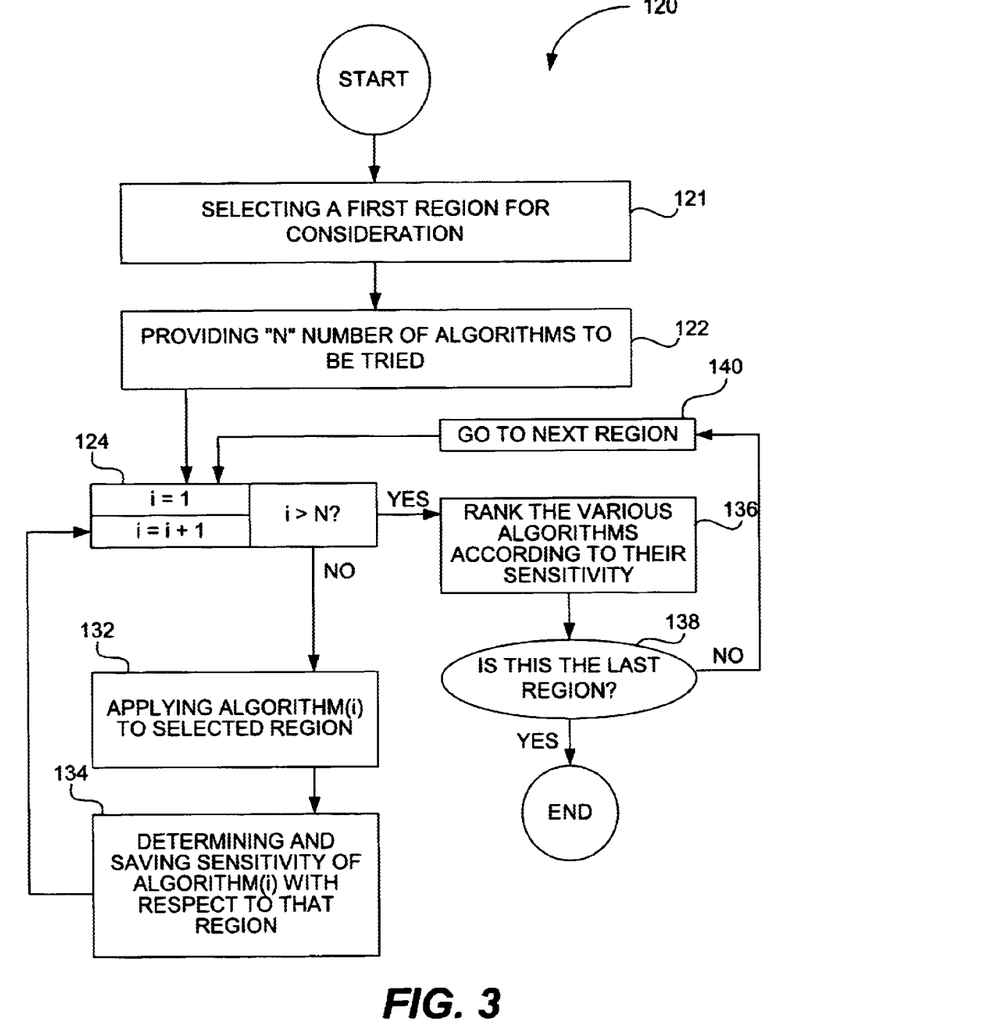
FIG. 3 shows a flowchart of a process, according to one embodiment of the present invention, of automatically determining which algorithms are best suited for generating an image of a particular region of a reticle.

FIG. 3 shows a process 120 of automatically mapping imaging algorithms to regions of the reticle. Preferably, this process is applied to the baseline image. Then, when the new image is being generated, the algorithms identified in process 120 are employed at the appropriate regions to generate the new image.

Process 120 begins at a step 121, which includes selecting a first region of the reticle. Next, in a step 122, "N" number of algorithms to be tried are selected or identified. Representative algorithms include mathematical functions that consider the intensity of scattered energy detected by a single detector, the difference in the intensity detected by two detectors, the optimum value for the predefined threshold of intensity of scattered energy, the average intensity of the surrounding pixels or regions, the difference between the intensities of two neighboring pixels or regions, the application of filter, etc.

The process of optimizing an algorithm for a specific region begins at an iterative loop step 124, in which "i" is an index denoting an initial algorithm index and "N" denotes the total number of algorithms that may apply to a region of the reticle. Iterative loop step 124 iterates from a value of i that starts at 1 and is terminated when i equals N.

In a step 132, an algorithm(i) is applied to the current region of the reticle. Next, in a step 134, the sensitivity of the algorithm with respect to that region is determined and saved in memory. The term "sensitivity" as used in connection with the description of this invention refers to the ability of the algorithm to distinguish between a real defect and a false defect. The iterative loop continues to consider additional algorithms, determining and saving their sensitivities, until N algorithms are applied to the region. Then, in a step 136, the various algorithms are ranked according to their sensitivity. It is important to note that sensitivity to real defects (e.g., contaminants, etc.) is relatively fixed and well established. This process determines sensitivity to "false defects."

Next, in step 138 it is determined whether the region under consideration is the last region. If so, the process is concluded. If not, the iterative loop described above proceeds to rank the algorithms according to their sensitivity for another region of the reticle. This process continues until all the regions are evaluated. In the end, the algorithms and their rank are saved in memory to facilitate future scans in effectively discerning between a real and false defect.

According to an alternative embodiment of process 120, index "i" as set forth in step 124 may refer to an initial machine setting index, instead of an initial algorithm index as described above. "Machine settings" as that term is used herein refers to the settings of the system that generates the scattering data. Examples of machine setting parameters include the intensity and orientation of the illuminating source, the orientation of the detectors, the filtering of the detectors, the incident light polarization, etc. Each machine setting parameter can be adjusted to better discriminate between real and false defects.

In one simple case, a first scan of the reticle is conducted with a detector oriented at a first angle with respect to an incident axis and the plane of the reticle. In a second scan, the detector is oriented at a second angle with respect to the incident axis and the reticle plane. Multiple such settings may be considered during the iterations set forth in process 120. For each region considered, the different machine settings can be ranked according to their sensitivity.

With reference to FIG. 2A, this embodiment may affect the implementation of step 110. Specifically, if step 104 is carried out in multiple passes (each with a different machine setting), step 110 should be carried out with the same group of passes. The results of one scan will be applied to a first group of image regions, the results of a second scan will be applied to a second group of image regions, etc. This will, of course, slow the imaging process, but in some cases will produce an overall better comparison of the baseline and new reticles.

Figure 4:
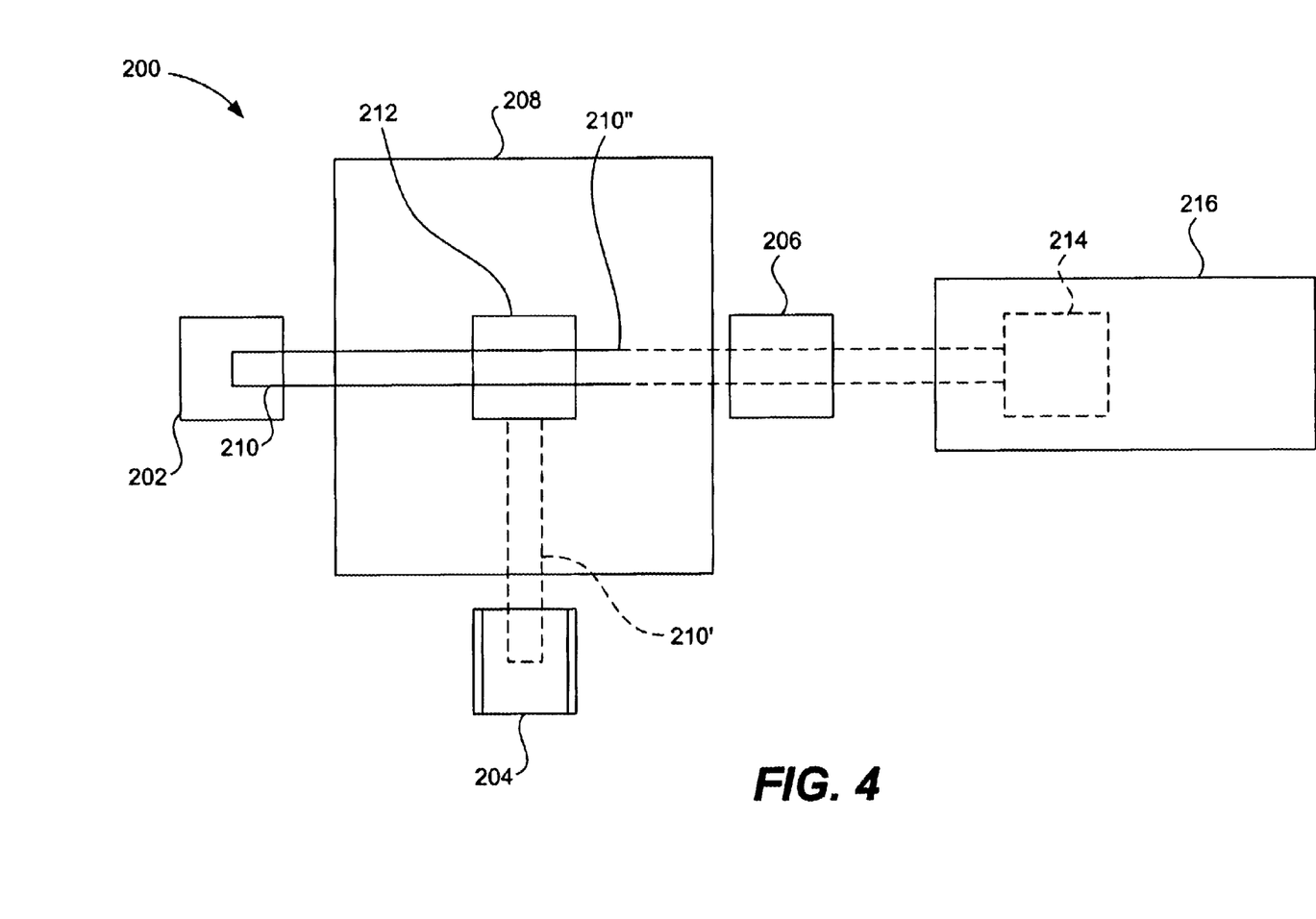
FIG. 4 shows a top view of a reticle inspection station and reticle stocker station where the process of FIG. 2A may be implemented in a preferred embodiment of the present invention.

FIG. 4 shows a reticle inspection station-reticle stocker station 200 where process 100 of FIG. 2A would be implemented in a preferred embodiment of the present invention. An autoloader 208 for automatically transporting reticles includes a robot 212 having an arm 210 extending towards a inspection port of a reticle inspection station. Arm 210 may rotate and can extend towards an external port 204 when in its state denoted by reference number 210'. Similarly, when in its state denoted by reference number 210", the robotic arm can also extend towards a storage port 206 of a reticle stocker station 216 that typically includes several slots or tracks for storing reticles. The robotic arm is designed to further extend and retrieve a reticle 214 from reticle stocker station 216.

A typical inspection process, according to one embodiment of the present invention, may begin after reticle 214 is qualified and placed on external port 204, with the intention of storing the reticle in reticle stocker station 216 until it is used in a subsequent conventional photolithography application, for example. Robotic arm in its position 210' transports the reticle from external port 204 and stores it in a loading port of reticle stocker station 216 by extending as shown in FIG. 4. When the reticle is needed for production, for example, robotic arm 210" retrieves reticle 214 from the loading port and places it on inspection port 202, where comparison phase 118 of FIG. 2A detailed above is carried out and it is determined whether new real defects have appeared in the reticle. After the reticle inspection has concluded, reticle 214 is placed on external port 204 so that it may be carried to a fabrication facility for use.

Those skilled in the art will appreciate that the vendor who has qualified the reticle may provide the end user of the reticle, e.g. a fabrication facility, with the baseline image of the reticle and perform the steps of baseline generation phase 116 detailed in FIG. 2A.

Suitable computer systems for use in implementing and controlling the methods in the present invention (e.g., controlling the settings of the various scanning apparatus components, storing baseline image of the reticle, segmenting the baseline image, compacting the baseline image, storing new image of the reticle, comparing the new image with the baseline image, storing the location of real and false defects, etc.) may be obtained from various vendors. In one preferred embodiment, an appropriately programmed HP735 workstation (Hewlett Packard, Palo Alto, Calif.) or Sun ULTRASPARC or Sun SPARC (Sun Microsystems, Sunnyvale, Calif.) may be employed. In any case, the computer system preferably has one or more processors coupled to input/output ports, and one or more memories via appropriate buses or other communication mechanisms.

Preferably, an illumination system such as illustrated in FIG. 1B is integrated with a computer system which implements many of the method steps of this invention. Such composite system preferably includes at least (a) a baseline image (preferably compacted) stored in a memory, (b) an imaging system arranged to generate a current image of the reticle, and (c) a processing unit configured to compare the baseline and current images and thereby identify any new defects that may have arisen in the time between when the baseline image was created and when the current image is generated. At a minimum, the imaging system will usually include (i) a source of illumination oriented to direct light onto a specified location of the reticle; and (ii) one or more detectors oriented to detect light from the source which has been scattered by the reticle. The imaging system may also include a scanning means.

It should be understood that the present invention also relates to machine readable media on which are stored instructions for implementing the invention. Such instructions facilitate the comparison of the baseline image with the new image of the reticle and the provision of optimizing algorithms, settings of the illuminating source or detectors based on a certain predetermined criteria. Such media includes, by way of example, magnetic disks, magnetic tape, optically readable media such as CD ROMs, semiconductor memory such as PCMCIA cards, etc. In each case, the medium may take the form of a portable item such as a small disk, diskette, cassette, etc., or it may take the form of a relatively larger or immobile item such as a hard disk drive or RAM provided in a computer.

The present invention described above represents a marked improvement over the current approaches of identifying the location of real defects in a reticle. By way of example, the present invention can effectively identify the location of real defects in a reticle containing the pattern for only a single die. As another example, the present invention identifies the location of real defects with significant accuracy and speed. As yet another example, the present invention can effectively find small real defects in the presence of large signals that are generated by die features that are not real defects.

Although the foregoing invention has been described in some detail for purposes of clarity of understanding, it will be apparent that certain changes and modifications may be practiced within the scope of the appended claims. For example, while the specification has described methods of identifying defects as applicable to reticle evaluation, there is no reason why, in principle, these methods of identifying defects cannot be applied to other objects that may become defective over time. For example, the invention could be applied to identify defects in other optical elements used in photolithography. Therefore, the present embodiments are to be considered as illustrative and not restrictive, and the invention is not to be limited to the details given herein, but may be modified within the scope of the appended claims.

What is claimed is:

1. A method for identifying a defect in a reticle containing features that scatter light, which features together define a pattern to be transferred a substrate surface, the method comprising:

providing a baseline image of said reticle which baseline image was created while the reticle was qualified as being of acceptable quality;

generating a current image of the reticle; and comparing the baseline and current images wherein the differences between these images identify defects that may have arisen in the time between when the baseline image was created and when the current image is generated.

2. The method of claim 1, wherein said features that scatter light include features that modulate light transmission.

3. The method of claim 2, wherein said features that scatter light include features that are opaque or transparent to light.

4. The method of claim 1, wherein the current image is generated by scanning said reticle to develop an image of said reticle.

5. The process of claim 4, wherein each pixel of the current image is generated by a method comprising:

illuminating a region of said reticle by an incident beam generated by an illuminating source;

detecting a scattered energy distribution from said region of said reticle by a detector; and recording said scattered energy distribution from said region of said reticle.

6. The process of claim 1, wherein comparing the baseline and current images includes:

determining whether intensity of scattered radiation at a first location of the current image is greater than a defined threshold;

if the scattered radiation from the first location is greater than the defined threshold, determining whether an absolute value of a difference between the intensity of scattered light at the first location and the intensity of scattered light in a corresponding region of the baseline image of the region exceeds a predefined deviation value; and if the absolute value of the difference between the intensity of scattered light at the first location and the intensity of scattered light in the corresponding region of the baseline image of the region exceeds a predefined deviation value, flagging a defect at the first location.

7. A method of inspecting an object, comprising:

(a) providing an object to be inspected;

(b) storing a baseline image of the object at a time when the object is known to be of acceptable quality;

(c) inspecting the object at a time when the object is not known to be of acceptable quality;

(d) comparing data derived from the inspection with data derived from the stored baseline image; and (e) identifying defects on the object based on the comparison.

8. The method of claim 7, wherein the object is a reticle.

9. The method of claim 7, wherein the stored baseline image contains data correlating the intensity of radiation scattered from the object with locations of the object.

10. The method of claim 9, wherein storing the baseline image includes compacting the baseline image to reduce the quantity of stored data for portions of the image where the intensity of the scattered radiation does not exceed a defined threshold.

11. The method of claim 10, wherein compacting includes the following:

segmenting the baseline image into regions of the object; and removing data from the baseline image for those regions of said object where the intensity of the scattered radiation does not exceed the defined threshold.

12. The method of claim 7, wherein the object is known to be of acceptable quality by subjecting it to an optical qualification technique.

13. The method of claim 8, wherein the object is known to be of acceptable quality by subjecting it to a method comprising:

electronically testing at least one die fabricated on al substrate by process employing and reticle; and determining whether said at least one die passes the testing, in which case the reticle is qualified.

14. The method of claim 7, wherein inspection is performed by generating a darkfield image of the object.

15. The method of claim 8, wherein inspection of the object includes measuring and recording scattered light from the object as a function of position on the reticle.

16. The method of claim 7, wherein defects are identified at locations wherein the inspection data and the baseline image data deviate from one another.

17. A method of providing a baseline image of a reticle for use in subsequent inspections of the reticle, comprising:

(a) providing the reticle to be inspected;

(b) generating data specifying intensity of radiation scattered from the reticle as a function of location on the reticle;

(c) defining a first portion of the data which was derived from a first region on the reticle;

(d) applying a plurality of imaging algorithms to the first portion of the data;

(e) selecting a first imaging algorithm from among the plurality of imaging algorithms based upon ability to suppress scattered radiation from valid features on the first region of the reticle; and (f) associating the first imaging algorithm with the first portion of data in the baseline image, such that during the subsequent inspections of the reticle the first imaging algorithm is applied to the first portion of the data to provide an image of the first region of the reticle.

18. The method of claim 17, further comprising ranking the plurality of imaging algorithms according to ability to suppress scattered radiation from valid features on the reticle.

19. The method of claim 17, further comprising storing in memory an association of the first imaging algorithm with the first region of the reticle.

20. The method of claim 17, wherein generating data specifying intensity of radiation comprises:

(i) carrying out a first scan of the reticle under a first apparatus setting for determining intensity of radiation scattered from the reticle as a function of location on the reticle;

(ii) carrying out a second scan of the reticle under a second apparatus setting which are different from the first apparatus setting;

(iii) selecting an apparatus setting based upon ability to suppress scattered radiation from valid features on the reticle.

21. The method of claim 20, wherein (iii) is performed for each of a plurality of regions of the reticle.

22. The method of claim 21, further comprising associating a selected apparatus setting with one or more regions of the reticle, such that during the subsequent inspections of the reticle data from the selected apparatus setting may be used to image the one or more regions.

23. A system for identifying a defect in a reticle containing transparent regions and opaque regions defining a pattern to be transferred a substrate surface, the system comprising:

a baseline image stored in a memory, the baseline image being an image of the reticle taken while the reticle was known to be of acceptable quality;

an imaging system arranged to generate a current image of the reticle, which current image corresponds to the baseline image; and a processing unit configured to compare the baseline and current images and thereby identify any new defects that may have arisen in the time between when the baseline image was created and when the current image is generated.

24. The system of claim 23, wherein the baseline image contains data correlating the intensity of radiation scattered from the object with locations of the object.

25. The system of claim 23, wherein the baseline image is compacted.

26. The system of claim 23, wherein the imaging system includes:

a source of illumination oriented to direct light onto a specified location of the reticle; and one or more detectors oriented to detect light from the source which has been scattered by the reticle.

* * * * *